(12) United States Patent
Gelboin et al.

(10) Patent No.: US 6,623,960 B1
(45) Date of Patent: Sep. 23, 2003

(54) AGENTS THAT BIND TO AND INHIBIT HUMAN CYTOCHROME P450 2C8, 2C9, 2C18 AND 2C19

(75) Inventors: Harry V. Gelboin, Chevy Chase, MD (US); Kristopher W. Krausz, Columbia, MD (US); Frank J. Gonzalez, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/469,655

(22) Filed: Dec. 22, 1999

Related U.S. Application Data
(60) Provisional application No. 60/119,972, filed on Feb. 12, 1999.

(51) Int. Cl.$^7$ .............................. C12N 5/06; C07K 16/00
(52) U.S. Cl. ..................... 435/326; 435/331; 435/333; 530/388.1; 530/388.15; 530/388.21
(58) Field of Search ................................. 435/7.1, 7.92, 435/338, 252.1, 326, 331, 333; 530/388.26, 388.21, 387.1, 388.15, 388.1

(56) References Cited

U.S. PATENT DOCUMENTS 5,939,530 A    8/1999  Gelboin et al.

OTHER PUBLICATIONS

Pierce Chemical Company catalogue. 1994. "Antibody Fragmentation". Rockford, IL.*
Rudikoff et al. PNAS. 1982; 79: 1979–1983.*
Sai et al., "An inhibitory monoclonal antibody to human cytochrome P450 2A6 defines its role in the metabolism of coumarin, 7–ethoxycoumarin and 4–nitroanisole in human liver," *Pharmacogenetics*, 9:229–237 (1999).
Shou et al., "Use of inhibitory monoclonal antibodies to assess the contribution of cytochromes P450 to human drug metabolism" *Eur. J. Pharmacol.*, 394(203):199–209, (2000).
Sullivan–Klose et al., The role of the CYP2C9–Leu359 allelic variant in the tolbutamide polymorphism, *Pharmacogenetics*, 6:341–349 (1996).
Veronese et al., Tolbutamide and phenytoin hydroxylation's by cDNA–expressed human liver cytochrome P450 2C9, *Biochemical Biophysical Research Comminations*, 175:1112–1118 (1991).
Washida et al., "Preparation of an activity–inhibiting monoclonal antibody against human placental aromatase cytochrome P450," *Steroids*, 61:126–132 (1996).
Yamazaki et al., "7–ethyloxycoumarin 0–deethylation catalyzed by cytochromes P450 1A2 and 2E1 in human liver microsomes," *Biochem. Pharmacol.*, 51:313–319 (1996).

Yamazaki et al., Comparative studies on the catalytic roles of cytochrome P450 2C9 and its Cys– and Leu–variants in the oxidation of warfarin, flurbioprofen, and diclofenac by human liver microsomes, *Biochem Pharmacol*, 56:243–251 (1998).
Yang et al., "Eight inhibitory monoclonal antibodies define the role of individual P–450s in human liver microsomal diazepam, 7–ethoxycoumarin and imipramine metabolism" *Drug Metab. Dispos.*, 27(1):102–109, (1999).
Yang et al., "Inhibitory monoclonal antibodies to human cytochrome P450 1A2: Analysis of phenacetin 0–deethylation in human liver," *Pharmagogenetics*, 8:375–382 (1998).
Eichelbaum et al., "Genetically determined differences in drug metabolism as a risk factor in drug toxicity" *Toxicology Letters*, 64/65:155–122 (1992).
Gelboin, H. V., "Cytochrome P450 and monoclonal antibodies," *Pharmacol Rev*, 45(4):413–453, (1993).
Gelboin et al., "Inhibitory and noninhibitory monoclonal antibodies to human cytochrome P450 2E1," *Chem Res Toxicol*, 9(6):1023–1030, (1996).
Gelboin et al., "Inhibitory and non–inhibitory monoclonal antibodies to human cytochrome P450 3A3/4," *Biochem Pharmacol*, 50(11):1841–1850, (1995).
Gelboin et al., "A monoclonal antibody inhibitory to human P450 2D6: a paradigm for use in combinatorial determination of individual P450 role in specific drug tissue metabolism," *Pharmacogenetics*, 7:469–477, (1997).
Gelboin et al., Methods in Molecular Biology: Cytochrome P450 Protocols, (Phillips and Shephard, eds.) pp. 227–237, Humana Press, (1998).
Goldfarb et al., "Cross–reactivity of thirteen monoclonal antibodies with ten vaccinia cDNA expressed rat, mouse and human cytochrome P450s," *Biochem Pharmacol*, 46:787–790, (1993).
Goldstein et al., "Evidence that CYP2C19 is the major (S)–mephenytoin 4'–hydroxylase in humans," *Biochemistry*, 33:1743–1752 (1994).
Gonzalez, F.J., "Cytochromes P450: Metabolic and Toxicological Aspects," (Ioannides, C., ed.) pp. 183–210, CRC Press (1996).

(List continued on next page.)

*Primary Examiner*—James Housel
*Assistant Examiner*—Shanon Foley
(74) *Attorney, Agent, or Firm*—Townsend and Townsend and Crew LLP

(57) ABSTRACT

The invention provides monoclonal antibodies to human cytochrome P450 2C8, 2C9, 2C18, and 2C19 having advantageous properties, including capacity substantially to inhibit enzyme activity of the various human cytochrome P450 2C family members and lack of specific binding to other human cytochromes P450. The binding agents of the invention are useful inter alia in methods for screening drugs for metabolism by cytochrome P450 2C family members, and in methods of screening individuals for a poor metabolizing individual human P450 2C family phenotypes.

9 Claims, 11 Drawing Sheets

Gonzalez et al., "Pharmacogenetic phenotyping and genotyping", *Clin. Pharmacokin*, 26(1):59–70 (1994).

Gonzalez et al., "Role of Human Cytochrome P–450s in Risk Assessment and Susceptibility to Environmentally Based Disease," *J. Toxicol. and Environmental Health*, 40:289–308, (1993).

Gonzalez et al., "Expression of mammalian cytochrome P450 using vaccinia virus," *Methods Enzymol*, 206:85–92 (1991a).

Gonzalez et al., "Expression of mammalian cytochrome P450 using baculovirus," *Methods Enzymol*, 206:93–99, (1991b).

Guengerich et al., "Oxidation of toxic and carcinogenic chemicals by human cytochrome P–450 enzymes," *Chem Res Toxicol*, 4(4):391–407, (1991).

Haining et al., Alleliac variants of human cytochrome P450 2C9: baculovirus–mediated expression, purification, structural characterization, substrate steroselectivity, and prochiral selectivity of the wild–type and 1359L mutant forms, *Arch Biochem Biophys*, 333:447–458, (1996).

Kupfer et al., "Mephenytuin hydrolation deficiency: Kinetics after repeated doses," *Clin. Pharmacol. Ther.*, 35:33 (1984).

Madsen et al., "Imipramine demethylation in vivo: Impact of CYP1A2, CYP2C19, and CYP3A4," *Clin. Pharmacol. Ther.*, 61:319–324 (1997).

Miners et al., "Cytochrome P452C9: An enzyme of major importance in human drug metabolism," *Br. J. Clin. Pharmacol*, 45:525–538 (1998).

Nasu et al., Genetic analysis of CYP2C9 polymorphism in a Japanese population, *Pharmacogenetics*, 7:405–409 (1997).

Rendic et al., "Human cytochrome P450 enzymes: a status report summarizing their reactions, substrates, inducers, and inhibitors," *Drug Metab. Rev*, 29:413–580, (1997).

Rettie et al., "Impaired (S)–warfarin metabolism catalyzed by the R144C allelic variant of CYP2C9," *Pharmacogenetics*, 4:39–42 (1994).

* cited by examiner

| MAb/P450 | P450 | | | | | | | |
|---|---|---|---|---|---|---|---|---|
| | 2C8 | 2C9*1 | 2C9*2 | 2C9*3 | 2C18 | 2C19 | *others |
| MAb 292-2-3 | - | - | - | - | - | - | - |
| MAb 592-2-5 | + | ++ | +++ | ++ | +++ | - | - |
| MAb 5-7-5 | ++ | ++ | +++ | ++ | + | ++ | - |
| MAb 5-1-5 | ++ | - | - | - | - | - | - |
| MAb 281-1-1 | ++ | ++ | - | - | - | - | - |
| MAb 763-15-20 | ++ | ++ | +++ | ++ | - | - | - |

*other P450's include 1A1, 1A2, 2A6, 2B6, 2D6, 2E1, 3A4, 3A5
(-) signifies no activity

FIG. 1

| Mab/P450 | P450 | | | | | | |
|---|---|---|---|---|---|---|---|
| | 2C8 | 2C9*2 | 2C9*1 | 2C18 | 2C19 | *other P450s |
| MAb 292-2-3 | 0 | 92.5 | 11.0 | 0 | 0 | 0 |
| MAb 592-2-5 | 0 | 90.8 | 80.6 | 82.0 | 0 | 0 |
| MAb 5-7-5 | 0 | 96.0 | 91.3 | 93 | 95 | 0 |
| MAb 5-1-5 | 96.0 | 0 | 0 | 0 | 0 | 0 |
| MAb 281-1-1 | 91.0 | 0 | 0 | 0 | 0 | 0 |
| MAb 763-15-5 | 0 | 90 | 88.2 | 30 | 0 | 0 |

FIG. 2

| MAb | P450 | | | |
|---|---|---|---|---|
| | 2C8 | 2C9₍C35H4₎(*2) | 2C18 | 2C19 |
| MAb 292-2-3 | 0 | 91 | 0 | 0 |
| MAb 592-2-5 | 0 | 88 | 66 | 0 |
| MAb 5-7-5 | 0 | 93 | 93 | 93 |
| MAb 5-1-5 | 91.6 | 0 | 0 | 0 |
| MAb 281-1-1 | 91.8 | 0 | 0 | 0 |

FIG. 3

| MAb | Immuno Binding | h2C8 | h2C9*1 | h2C9*2 | h2C9*3 | h2C18 | h2C19 | Inhibits |
|---|---|---|---|---|---|---|---|---|
| MAb 292-2-3 | ELISA | - | - | +++ | - | - | - | 2C9*2 |
| | IB | - | - | - | - | - | - | |
| MAb 592-2-5 | ELISA | - | ++ | +++ | ++ | + | - | 2C9/18 |
| | IB | - | ++ | +++ | ++ | +++ | - | |
| MAb 5-7-5 | ELISA | - | ++ | +++ | ++ | +++ | +++ | 2C9/18/19 |
| | IB | + | ++ | +++ | ++ | + | ++ | |
| MAb 5-1-5 | ELISA | ++ | - | - | - | - | - | 2C8 |
| | IB | ++ | - | - | - | - | - | |
| MAb 281-1-1 | ELISA | ++ | - | - | - | - | - | 2C8 |
| | IB | ++ | - | - | - | - | - | |

FIG. 4

2C9 ALLELE^

| Substrate | *1 – WT Arg144 | | | *2 – Arg144Cys | | | *3 – Ile359Leu | | |
|---|---|---|---|---|---|---|---|---|---|
| | Control | +MAb | % Inh | Control | +MAb | % Inh | Control | +MAb | % Inh |
| Tolbutamide | 1.0 | 0.98 | 1.3 | 0.85 | 0.03 | 96.4 | 0.22 | 0.02 | 9.3 |
| Diclofenac | 0.3 | 0.3 | 0.1 | 0.42 | 0.02 | 95.1 | 0.35 | 0.30 | 14.4 |

^P450 activity is (nmolproduct/min/nmolP450)

FIG. 7

| Mab clone | 2C9 Arg144 | 2C9 Cys144 | 2C9 Arg144 Leu359 |
|---|---|---|---|
| 763-15-5 | 77.4% | 93.2% | 77.3% |
| 763-15-20 | 5.5% | 11.2% | 0.2% |

% Inhibition of enzyme

FIG. 11

AGENTS THAT BIND TO AND INHIBIT HUMAN CYTOCHROME P450 2C8, 2C9, 2C18 AND 2C19

CROSS-REFERENCES TO RELATED APPLICATIONS

This application claims the benefit of U.S. Provisional Application No. 60/119,972 filed Feb. 12, 1999, the disclosure of which is incorporated by reference.

STATEMENT AS TO RIGHTS TO INVENTIONS MADE UNDER FEDERALLY SPONSORED RESEARCH AND DEVELOPMENT

TECHNICAL FIELD

The present invention resides in the technical fields of immunology and enzymology.

BACKGROUND OF THE INVENTION

The cytochrome P450 family of enzymes is primarily responsible for the metabolism of xenobiotics such as drugs, carcinogens and environmental chemicals, as well as several classes of endobiotics such as steroids and prostaglandins. Members of the cytochrome P450 family are present in varying levels and their expression and activities are controlled by variables such as chemical environment, sex, developmental stage, nutrition and age.

More than 200 cytochrome P450 genes have been identified. There are multiple forms of these P450 and each of the individual forms exhibit degrees of specificity towards individual chemicals in the above classes of compounds. In some cases, a substrate, whether it be drug or carcinogen, is metabolized by more then one of the cytochromes P450.

Cytochrome P450 2C series of enzyme are of major importance in the use of drugs for the treatment of various disease conditions. The 2C family ranks among the most important of all of the P450 enzymes in humans.

Human cytochrome P450 2C9 is of major importance being responsible for the metabolism of numerous drugs and non-drug xenobiotics including tolbutamide, S-warfarin, phenytoin, diclofenac, ibuprofen, and losarten. The three major alleles of P450 2C9 are the wild type $2C9_{Arg144}(*1)$, $2C9_{Cys144}(*2)$, $2C9_{Ile \to Leu359}(*3)$ (Haining et al. 1996, Miners and Birkett 1998; hereinafter referred to as 2C9*1, 2C9*2 and 2C9*3 respectively). A genetic study of the 2C9 polymorphism indicated that the frequency of the 2C9* 1 and 2C9*3 alleles in a Caucasian American Population sere 0.08% and 0.06% respectively and 0.005 and 0.01% respectively in Afro-Americans (Sullivan-Klose et al. 1996). In a Japanese population the 2C9*2 allele was absent and the frequency of 2C9*3 was 0.021 (Nasu et al. 1997). In another study of 100 Caucasians the allelic frequency for the 2C9 wild type, 2C9*1, 2C9*2 and 2C9*3 were 0.79, 0.12 and 0.085 respectively (Stubbins et al. 1996).

The catalytic roles of the 2C9*1, 2C9*2 and 2C9*3 for the metabolism of warfarmn, flurbuprofen and diclofenac were studied in liver microsomes from 30 humans that were genotyped for the three 2C9 alleles. Nineteen of the humans were wild type, eight were heterozygous 2C9*2 and three were heterozygous for 2C9*3. All of the individuals with the 2C9*2 allele had similar but slightly lower activities for the metabolism of the three substrates. One of the three samples from heterozygotes for 2C9*3 had low $V_{max}$ and high $K_m$ while the other two samples were comparable to that of the 2C9*1 wild type and the 2C9*2. The conclusion of the study was that the 2C9*2 allele exhibited comparable but slightly lower metabolic activity than the wild type and the 2C9*3 had slower rates of oxidation compared to the wild type (Yamazaki et al. 1998). In another study (Veronese et al. 1991) found that the $V_{max}$ for the 2C9*2 allele for tolbutamide and phenytoin metabolism were 2–3 lower than the wild type 2C9. In a different study the $V_{max}$ of (S)7-hydroxy warfarmn formation was 20-fold greater in the wild type than the 2C9*2. The $V_{max}$ for methyihydroxy tolbutamide formation however was similar in the wild type and the 2C9*2 allelic (Rettie et al. 1994).

Typical substrates for 2C family members include taxol, tobutamide, pheytoin, lansoprazolem mephytoin, arachidonic acid, cyclophosphamide, ifosphamide, debrisoquine, methoxylflurane, tienilic acid, phenanthrene tolbutamide, benzo(a)pyrene, 58C80 (2-(4-t-Butylcyclohexhl)-3-hydroxyl-1,4-naphthoquinone), torsemide, aracidonic acid, mephenytoin, 1-tetrahydrocannabinol, and warfarin.

Genetic polymorphisms of cytochromes P450 result in phenotypically-distinct subpopulations that differ in their ability to perform biotransformations of particular drugs and other chemical compounds. These phenotypic distinctions have important implications for selection of drugs. For example, a drug that is safe when administered to most humans may cause toxic side-effects in an individual suffering from a defect in an enzyme required for detoxification of the drug. Alternatively, a drug that is effective in most humans may be ineffective in a particular subpopulation because of lack of a enzyme required for conversion of the drug to a metabolically active form. Further, individuals lacking a biotransformation enzyme are often susceptible to cancers from environmental chemicals due to inability to detoxify the chemicals. Eichelbaum et al., Toxicology Letters 64/65, 155–122 (1992). Accordingly, it is important to identify individuals who are deficient in a particular P450 enzyme, so that drugs known or suspected of being metabolized by the enzyme are not used, or used only with special precautions (e.g., reduced dosage, close monitoring) in such individuals. Identification of such individuals may indicate that such individuals be monitored for the onset of cancers.

Existing methods of identifying deficiencies in patients are not entirely satisfactory. Patient metabolic profiles are often assessed with a bioassay after a probe drug administration. Poor metabolizers (PM) exhibit physiologic accumulation of unmodified drug and have a high metabolic ratio of probe drug to metabolite. This bioassay has a number of limitations: Lack of patient cooperation, adverse reactions to probe drugs, and inaccuracy due to coadministration of other pharmacological agents or disease effects. See, e.g., Gonzalez et al., Clin. Pharmacokin. 26, 59–70 (1994). Genetic assays by RFLP (restriction fragment length polymorphism), ASO PCR (allele specific oligonucleotide hybridization to PCR products or PCR using mutant/wild-type specific oligo primers), SSCP (single stranded conformation polymorphism) and TGGE/DGGE (temperature or denaturing gradient gel electrophoresis), MDE (mutation detection electrophoresis) are time-consuming, technically demanding and limited in the number of gene mutation sites that can be tested at one time.

A complication in patient drug choice is that most drugs have not been characterized for their metabolism by P450 2C family and other cytochromes P450. Without knowing which cytochrome(s) P450 is/are responsible for metabolizing an individual drug, an assessment cannot be made for the adequacy of a patient's P450 profile. For such drugs, there is a risk of adverse effects if the drugs are administered to poor metabolizers.

Monoclonal antibodies that specifically bind to 2C family members and inhibit its activity, if available, could be used to screen drugs for their metabolism by 2C and/or identify 2C poor metabolizers by simple bioassays, thereby overcoming the problems in prior complicated methods discussed above. However, such monoclonal antibodies represent, at best, a small subset of the total repertoire of antibodies to human cytochrome P450 2C, and have not hitherto been isolated. Although in polyclonal sera, many classes of antibody may contribute to inhibition of enzyme activity of P450 2C family members as a result of multiple antibodies in sera binding to the same molecule of enzyme, only a small percentage of these, if any, can inhibit as a monoclonal. A monoclonal antibody can inhibit only by binding in such a manner that it alone block or otherwise perturb the active site of an enzyme. The existence and representation of monoclonal antibodies with inhibitory properties thus depend on many unpredictable factors. Among them are the size of the active site in an enzyme, whether the active site is immunogenic, and whether there are any sites distil to the active site that can exert inhibition due to stearic effects of antibody binding. The only means of obtaining antibodies with inhibitory properties is to screen large numbers of hybridoma until one either isolates the desired antibody or abandons the task through failure.

Notwithstanding these difficulties, the present invention provides inter alia monoclonal antibodies that specifically bind to human cytochrome P450 2C family members and inhibit their activity.

SUMMARY OF THE INVENTION

The invention provides isolated binding agents that compete with a monoclonal antibody MAb 292-2-3 for specific binding to human cytochrome P450 allelic variant 2C9*2 without specifically binding to human cytochrome 2C9*1 and 2C9*3, and that specifically inhibits 2C-catalyzed metabolism of phenanthrene by at least 50%. The invention further provides other isolated binding agents that compete with a monoclonal antibody MAb 763-15-5 for specific binding to the human cytochrome p450 2C9 allelic variants 2C9*1, 2C9*2, and 2C9*3, and that specifically inhibits 2C-catalyzed metabolism of phenanthrene by at least 50%. The invention further provides isolated binding agents that compete with a monoclonal antibody MAb 763-15-20 for specific binding to the human cytochrome P450 2C9 allelic variants 2C9*1, 2C9*2, and 2C9*3. The invention further provides isolated binding agents that compete with a monoclonal antibody MAb 592-2-5 for specific binding to human cytochrome P450 2C9 and 2C18, and that specifically inhibits 2C-catalyzed metabolism of phenanthrene by at least 50%. The invention further provides isolated binding agents that compete with a monoclonal antibody MAb 5-7-5 for specific binding to a human cytochrome p450 2C family member selected from the group consisting of 2C9, 2C18, and 2C19, and that specifically inhibits 2C-catalyzed metabolism of phenanthrene by at least 50%.

Preferred binding agents are monoclonal antibodies. Some binding agents lack specific binding to at least one cytochrome P450 selected from the group consisting of human cytochromes P450 1A1, 2A6, 2B6, 2C8, 2C9, 2C18, 2C19, 2D6, 2E1, 3A4, and 3A5. Some binding agents lack specific binding to each of human cytochromes P450 1A1, 2A6, 2B6, 2C8, 2C9, 2C18, 2C19, 2D6, 2E1, 3A4, and 3A5. Preferred binding agents are able to specifically inhibit the enzyme activity of human cytochrome P450 allelic variant 2C9*2 by at least 90%. Other preferred binding agents are able to specifically inhibit the enzyme activity of human cytochrome P450 allelic variant 2C9*2 by at least 70%. Other preferred binding agents are able to specifically inhibit the enzyme actibity of human cytochrome P450 allelic variants 2C9*1 and 2C9*3 by at least 70%. Some binding agents are binding fragments, such as Fab fragments.

MAb 292-2-3, MAb 592-2-5, MAb 5-7-5, MAb 5-1-5, MAb 281-1-1, MAb 763-15-5, and MAb 763-15-20 are exemplified monoclonal antibodies. Some other monoclonal antibodies are analogs of these monoclonal antibodies comprising a light chain variable domain having at least 80% sequence identity with the light chain variable domain of a monoclonal antibody selected from the group consisting of MAb 292-2-3, MAb 592-2-5, MAb 5-7-5, MAb 5-1-5, MAb 281-1-1, MAb 763-15-5, and MAb 763-15-20, wherein the percentage sequence identity is determined by aligning amino acids in the light chain variable domains by the Kabat numbering convention and a heavy chain variable domain having at least 80% sequence identity with the heavy chain variable domain of a monoclonal antibody selected from the group, wherein the percentage sequence identity is determined by aligning amino acids in the heavy chain variable domains by the Kabat numbering convention.

The invention further provides cell lines producing monoclonal antibodies as described above. Cells lines can be eucaryotic or procaryotic.

The invention further provides methods of determining whether a cytochrome P450 2C family member metabolizes a compound. Such methods entail contacting the compound with cytochrome P450 2C family member in the presence of varying amounts of the binding agents above. Metabolism of the compound is then assayed as a function of amount of binding agent, a decrease of metabolism with amount of binding agent indicating that cytochrome P450 2C family member metabolizes the compound. In some such methods, the compound is contacted with cytochrome P450 2C family member in a sample containing a collection of cytochrome P450 enzymes including the 2C family member. Preferred P450 2C family members are P450 2C9*1, 2C9*2, 2C9*3, 2C8, 2C18, and 2C19.

In some methods, the sample is a tissue sample. In some methods, the collection of enzymes are obtained from a cell culture expressing the enzymes. In some methods, the compound is a drug, steroid or carcinogen.

The invention further provides methods of detecting cytochrome P450 2C members. Such methods entail contacting a sample suspected of containing cytochrome P450 2C family member with a binding agent described above. One then determines whether the agent specifically binds to the sample, specific binding indicating the presence of the particular cytochrome P450 2C family member in the sample.

The invention further provides methods of measuring P450 2C levels in an individual relative to P450 levels in a control population. Such methods entail contacting a sample suspected of containing cytochrome a P450 2C family member from the individual and a substrate of 2C. One then determines the P450 2C levels in the individual relative to P450 2C levels in the control population.

BRIEF DESCRIPTION OF THE DRAWINGS

FIG. 1 Immunoblot analysis of expressed human P450s with MAb 592-2-5, MAb 5-7-5, MAb 5-1-5, MAb 281-1-1, and MAb 292-2-3.

FIG. 2 Inhibition of phenanthrene metabolism by monoclonal antibodies MAb 292-2-3, MAb 592-2-5, MAb 5-7-5, MAb 5-1-5, and MAb 281-1-1 to human P450 2C family members. The incubation and separation were performed as referenced (Shou et al., 1994).

FIG. 3 Inhibition of diazepam metabolism by monoclonal antibodies MAb 292-2-3, MAb 592-2-5, MAb 5-7-5, MAb 5-1-5, and MAb 281-1-1 to human P450 2C family members.

FIG. 4 Specificity analysis of MAb 292-2-3, MAb 592-2-5, MAb 5-7-5, MAb 5-1-5, and MAb 281-1-1 to human P450 2C family members. Immunoblots, ELISA, and inhibition results are shown.

FIG. 7. Tolbutamide and Diclofenac Metabolism by 2C9: Specific Inhibition of the P450 $2C9_{Cys\ 144}$(*2) Allele by MAb 292-2-3.

FIG. 11. Inhibition of P450 2C9 Allele Metabolism of Diclofenac.

DEFINITIONS

Figure 5:
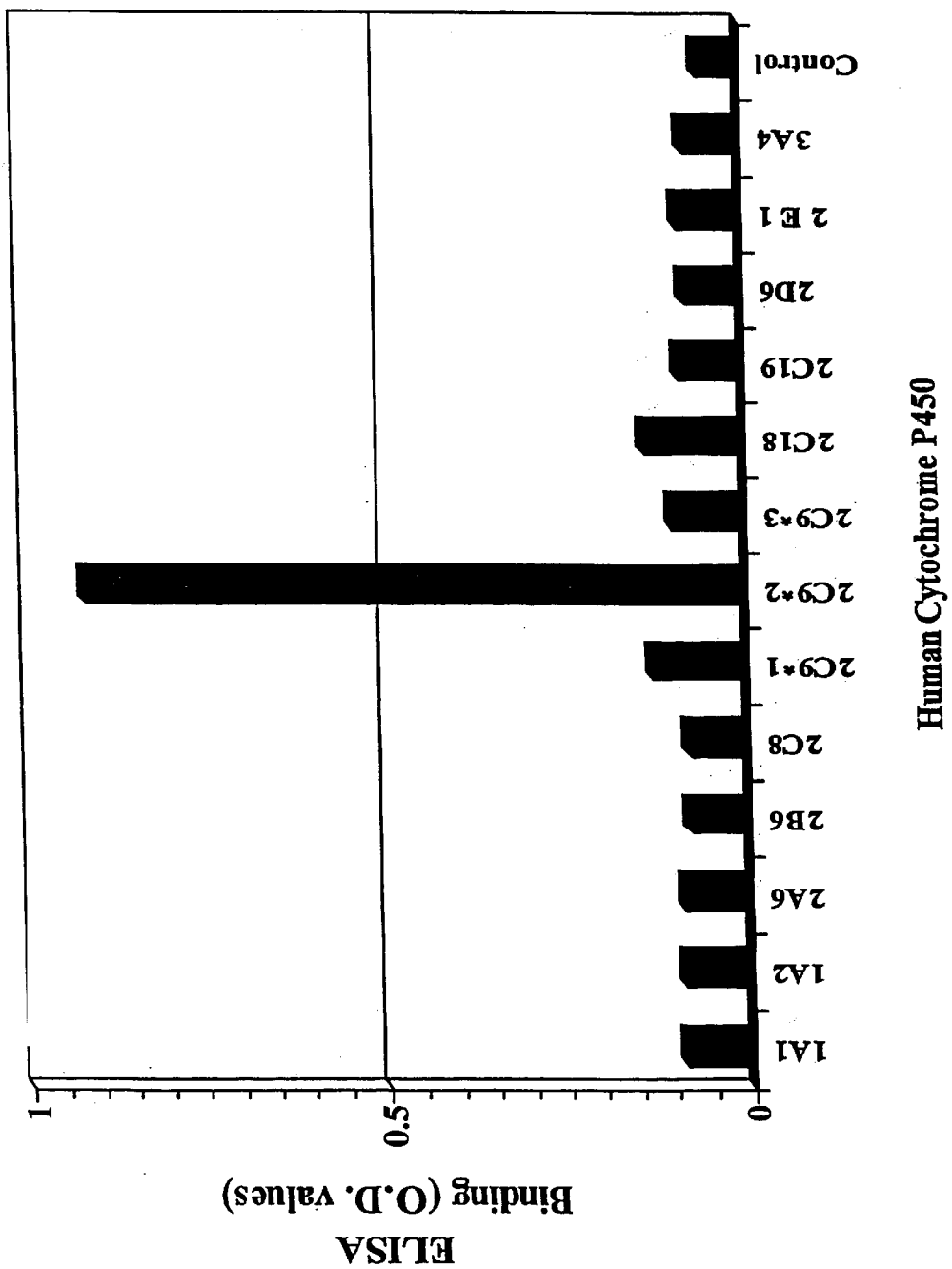
FIG. 5. Specificity of Binding of Monoclonal Antibody 292-2-3 to Expressed Human P450 Family Members.

Specific binding between an antibody or other binding agent and an antigen means a binding affinity of at least $10^6$ $M^{-1}$. Preferred binding agents bind human cytochrome P450 2C family members with affinities of at least about $10^7$ $M^{-1}$, and preferably $10^8$ $M^{-1}$ to $10^9$ $M^{-1}$ or $10^{10}$ $M^{-1}$. Lack of specific binding means a binding affinity of less than $10^6$ $M^{-1}$.

Lack of inhibition means that P450 metabolism in the presence of an excess of antibody is inhibited by less than 10% of the value in the absence of antibody.

The term epitope means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The phrase "substantially identical," in the context of two nucleic acids or polypeptides (e.g., DNAs encoding a humanized immunoglobulin or the amino acid sequence of the humanized immunoglobulin) refers to two or more sequences or subsequences that have at least about 80%, most preferably 90–95% or higher nucleotide or amino acid residue identity, when compared and aligned for maximum correspondence, as measured using the following sequence comparison method and/or by visual inspection. Such "substantially identical" sequences are typically considered to be homologous. Preferably, the "substantial identity" exists over a region of the sequences that is at least about 50 residues in length, more preferably over a region of at least about 100 residues, and most preferably the sequences are substantially identical over at least about 150 residues, or over the fall length of the two sequences to be compared. As described below, any two antibody sequences can only be aligned in one way, by using the numbering scheme in Kabat. Therefore, for antibodies, percent identity has a unique and well-defined meaning. That is, percent sequence identity is the percentage of aligned amino acids or nucleotides that are the same between two immunoglobulins or their coding sequences being compared.

Amino acids from the variable regions of the mature heavy and light chains of immunoglobulins are designated Hx and Lx respectively, where x is a number designating the position of an amino acids according to the scheme of Kabat et al., Sequences of Proteins of Immunological Interest (National Institutes of Health, Bethesda, Md. (1987) and (1991)) Kabat et al. list many amino acid sequences for antibodies for each subclass, and list the most commonly occurring amino acid for each residue position in that subclass. Kabat et al. use a method for assigning a residue number to each amino acid in a listed sequence, and this method for assigning residue numbers has become standard in the field. Kabat et al's scheme is extendible to other antibodies not included in the compendium by aligning the antibody in question with one of the consensus sequences in Kabat et al. The use of the Kabat et al. numbering system readily identifies amino acids at equivalent positions in different antibodies. For example, an amino acid at the L50 position of a human antibody occupies the equivalence position to an amino acid position L50 of a mouse antibody.

The term antibody is used to mean whole antibodies and binding fragments thereof.

An isolated species means an object species (e.g., a binding polypeptide of the invention) that is the predominant species present (i.e., on a molar basis it is more abundant than any other individual species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods).

DETAILED DESCRIPTION

The invention provides monoclonal antibodies and other binding agents in isolated form that specifically bind to human cytochrome P450 2C8, 2C9*1, 2C9*2, 2C9*3, 2C18, and 2C19, and inhibit enzymic activity of these human cytochromes. Preferred agents lack specific binding to other human cytochromes P450. The invention further provides methods of using the antibodies and other binding agents in identifying individuals with a poor metabolizing 2C family member phenotypes, and in screening drugs for metabolism by cytochrome P450 2C family members.

I. Binding Agents of the Invention

A. Specificity and Functional Properties

Binding agents of the invention compete with exemplary antibodies designated MAb 292-2-3 (ATCC HB-12645), MAb 592-2-5 (ATCC-12646), MAb 5-7-5 (ATCC-12647), MAb 5-1-5 (ATCC HB-12649), MAb 281-1-1 (ATCC HB-12648), MAb 763-15-5 (ATCC PTA-1079), and MAb 763-15-20 (ATCC PTA-1078), for specific binding to human cytochrome P450 2C family members. Production of monoclonal antibodies MAb 292-2-3, MAb 592-2-5, MAb 5-7-5, MAb 5-1-5, MAb 281-1-1-1, MAb 763-15-5, and MAb 763-15-20 is described in the Examples.

1. MAb 292-2-3, MAb 763-15-5, and MAb 763-15-20

The data in the Examples show that Mab 292-2-3 specifically binds only to the single expressed human P450 $2C9_{Cys\ 144}$(*2) and does not bind the wild type human P450

2C9$_{Arg\ 144}$(*1) or the human P450 2C9*3. MAb 292-2-3 inhibits the enzyme activity of P450 2C9$_{Cys\ 144}$(*2) by more than 90% as measured with phenanthrene metabolism. MAb 292-2-3 does not inhibit the enzyme activity of the other two P450 2C9 alleles, the P450 2C family members 2C8, 2C18, 2C19, or human P450 1A1, 1A2, 2A6, 2B6, 2D6, 2E1, 3A4, and 3A5. MAb 292-2-3 does not immunoblot P450 2C9$_{Cys\ 144}$(*2), 2C9$_{Arg\ 144}$(*1), or 2C9*3, 2C8, 2C18, 2C19, human P450 1A1, 1A2, 2A6, 2B6, 2D6, 2E1, 3A4, and 3A5. MAb 292-2-3 identifies and determines the quantitative amount of a drug substrate metabolized by P450 2C9$_{Cys\ 144}$(*2) and therefore its role in drug metabolism.

MAb 763-15-5 specifically inhibits all three 2C9 allelic variants. MAb 763-15-5 specifically inhibits the enzyme activity of P450 2C9$_{Arg\ 144}$(*1) by more than 85%; specifically inhibits the enzyme activity of P450 2C9$_{Cys\ 144}$(*2) by more than 90%; and specifically inhibits the enzyme activity of P450 2C9*3 by more than 75%, as measured by phenanthrene, bufuralol, or diclofenac metabolism. MAb 763-15-5 also inhibits human P450 2C18 by 30% as measured by phenanthrene metabolism. MAb 763-15-5 does not immunoblot any of the P450 2C9 alleles, 2C8, 2C18, 2C19, human P450 1A1, 1A2, 2A6, 2B6, 2D6, 2E1, 3A4, and 3A5.

MAb 763-15-20 immunoblots all three human P450 2C9 alleles as well as human P450 2C8. Mab 763-15-20 does not immunoblot P450 2C18, 2C19, 1A1, 1A2, 2A6, 2B6, 2D6, 2E1, 3A4, and 3A5. Human P450 2C8 can be distinguished by its large difference in migration relative to the human P450 2C9 family. At very high concentrations (greater than in normal use) a slight band is observed with human P450 2C19.

2. Mab 5-1-5 and MAb 281-1-1

MAb 5-1-5 and MAb 281-1-1 specifically inhibit the enzyme activity of human P450 2C8 as measured with phenanthrene, diazepam and taxol metabolism. MAb 5-1-5 and MAb 281-1-1 do not inhibit the enzyme activity of the other P450 2C family members 2C9, 2C18, 2C19 or human P450 1A1, 1A2, 2A6, 2B6, 2D6, 2E1, 3A4, and 3A5.

MAbs 281-1-1 and 5-1-5 yield an immunoblot only to the target 2C8 and not to the other P450 members. The immunoblot data further indicates that these antibodies bind to epitope(s) that are not lost on treatment with a denaturing solvent. Both MAbs 281-1-1 and 5-1-5 identify drug substrates for human P450 2C8, determine the amount of 2C8 protein present in a sample, and its role in drug metabolism.

3. MAb 592-2-5

MAb 592-2-5 specifically forms an immunoblot and inhibits the enzyme activity of human P450 2C9 and 2C18. These two antibodies do not inhibit the enzyme activity of the other P450 2C family members 2C8 and 2C19 or human P450 1A1, 1A2, 2A6, 2B6, 2D6, 2E1, 3A4, and 3A5.

4. MAb 5-7-5

MAb 5-7-5 inhibits the enzyme activity of 2C9/18/19 but not 2C8 and the other P450. MAb 5-7-5 yields a strong immunoblot with 2C9 and a weak to moderate immunoblot to 2C8, 2C18, and 2C19. FIG. 4 provides a summary of results with the MAbs of the invention to each of the 2C family P450 for ELISA, immunoblot and enzyme inhibition studies.

Hybridomas producing MAb 292-2-3 (ATCC HB-12645), MAb 592-2-5 (ATCC HB-12646), MAb 5-7-5 (ATCCHB-12647), MAb 5-1-5 (ATCC-HB 12649), MAb 281-1-1 (ATCC HB-12[4]648), MAb 763-15-5 (ATCC PTA-1079), and MAb 763-15-20 (ATCC PTA-1078) have been deposited with the American Type Culture Collection, 10801 University Boulevard, Manassus, Va. 20110-2209 nder the Budapest Treaty and given the Accession Nos. indicated.

MAb 292-2-3 (ATCC HB-12645), MAb 592-2-5 (ATCC HB-12646), MAb 5-7-5 (ATCCHB-12647), MAb 5-1-5 (ATCC HB-12649), MAb 281-1-1 (ATCC HB-12648) were given the Accession Nos. indicated on Feb. 3, 1999. MAb 763-15-5 (ATCC PTA-1079), and MAb 763-15-20 (ATCC PTA-1078) were given the Accession Nos. indicated on Dec. 21, 1999. These cell lines will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

Competition is determined by an assay in which the antibody under test inhibits specific binding of a reference antibody to an antigenic determinant on human cytochrome P450 2C family members. Numerous types of competitive binding assays are known for example: (see Harlow and Lane, "Antibodies, A Laboratory Manual," Cold Spring Harbor Press (198)). Typically, such an assay involves the use of a purified human cytochrome P450 2C family member, an unlabelled test antibody and a labeled reference antibody. Competitive inhibition is measured by determining the amount of label bound to the human cytochrome P450 2C family member in the presence of the test antibody. Usually the test antibody is present in excess. Antibodies identified by competition assay (competing antibodies) include antibodies binding to the same epitope as a reference antibody and antibodies binding to an adjacent epitope sufficiently proximal to the epitope bound by the reference antibody for steric hindrance to occur. Usually, when a competing antibody is present in excess, it will inhibit specific binding of a reference antibody to the human cytochrome P450 2C family member by at least 10, 25, 50 or 75%.

Binding agents of the invention typically lack specific binding (i.e., crossreactivity) to human cytochromes P450 other than the individual 2C family members, so that the binding agents can be used to detect human cytochrome P450 2C family members in the presence of other cytochromes P450. For example, binding agents of the invention typically lack specific binding to one or more of human cytochromes P450 1A1, 1A2, 2A6, 2B6, 2C8, 2C9, 2C18, 2C19, 2D6, 2E1, 3A4, and 3A5 as measured by ELISA and immunoblot. Some binding agents of the invention, including the exemplified monoclonal antibodies of the invention lack specific binding to some or all of the above human cytochromes P450.

As noted above, binding agents of the invention are characterized by capacity to inhibit a particular human cytochrome P450 2C family member-catalyzed metabolism of a substrate known to be metabolized by the enzyme. The enzyme can be assayed with any of diazepam, taxol, and phenanthrene (see present Examples). Assays can be performed in either a microsome systems or a reconstituted systems of purified enzymes. For example, a suitable microsome system contains 1 mg/ml protein of human liver microsomes or 1.6 mg protein/ml from human lymphoblast cell lines, together with 0.2 mM substrate in a final volume of 1.0 ml of 100 mM potassium phosphate buffer, pH 7.5, and 1 mM NADPH. An exemplary reconstituted system, in place of the microsome system, contains about 20–50 nM a purified human P450 2C family member, 40–100 nM cytochrome b5, 100 nM NADPH-P450 reductase, 10 $\mu$Ag/ml phospholipids and 0.25 mM sodium cholate. Incubations are typically carried out at 37° C. for 30 min. Percentage inhibition is defined as 1—(rate of formation metabolic product in presence of test antibody/rate of formation of metabolic product in presence of control antibody), when antibody is present in excess. (The control antibody is an antibody lacking specific binding to the particular human cytochrome P450 2C family member being studied.) Some agents of the invention inhibit metabolic capacity of isolated pure cytochrome P450 2C family members on any or all of the above substrates by at least 25%, 50%, 75%, 85%, 90% or 95%.

B. Antibodies of the Invention

1. General Characteristics

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology (Paul, W., ed., 2nd ed. Raven Press, N.Y., 1989), Ch. 7 (incorporated by reference in its entirety for all purposes).

The variable regions of each light/heavy chain pair form the antibody binding site. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. CDR and FR residues are delineated according to the standard sequence definition of Kabat et al., supra. An alternative structural definition has been proposed by Chothia et al., J. Mol. Biol. 196, 901–917 (1987); Nature 342, 878–883 (1989); and J. Mol. Biol. 186, 651–663 (1989).

2. Production

Antibodies to human cytochrome P450 2C family members can be produced by a variety of means. The production of non-human monoclonal antibodies, e.g., murine or rat, can be accomplished by, for example, immunizing the animal with a preparation containing purified human cytochrome P450 or a fragment thereof. The immunogen can be obtained from a natural source, by peptides synthesis or preferably by recombinant expression. Antibody-producing cells obtained from the immunized animals are immortalized and screened for the production of an antibody which binds to human cytochrome P450 or a fragment thereof. See Harlow & Lane, Antibodies, A laboratory Manual (CSHP NY, 1988) (incorporated by reference for all purposes).

A cloned human P450 2C cDNA family member of interest can be inserted into a baculovirus vector and Hi-five or Spondoptera Frugipedra (Sf9) cells (or other suitable cell line) can be infected with the recombinant baculovirus to produce the particular 2C family member (e.g., see Buters et al., 1994; Gonzalez et al., 1991b). BALB/c mice can then be immunized by i.p. injection weekly for 3 weeks with 30 mg of the particular 2C family member of interest protein emulsified in complete Freund's adjuvant for the first injection, and then with incomplete Freund's adjuvant for subsequent injections. Three days after the third injection, the mouse serum can be examined by ELISA. The mice are sacrificed and spleens removed. The hybridoma production, screening by ELISA and IB of MAbs, and MAb content determination are the same described (Gelboin et al., 1996; Gelboin et al., 1995).

Humanized forms of mouse antibodies can be generated by linking the CDR regions of non-human antibodies to human constant regions by recombinant DNA techniques. See Queen et al., Proc. Natl. Acad. Sci. USA 86, 10029–10033 (1989) and WO 90/07861 (incorporated by reference for all purposes).

Human antibodies can be obtained using phage-display methods. See, e.g., Dower et al., WO 91/17271; McCafferty et al., WO 92/01047. In these methods, libraries of phage are produced in which members display different antibodies on their outersurfaces. Antibodies are usually displayed as $F_v$, or Fab fragments. Phage displaying antibodies with a desired specificity are selected by affinity enrichment to human cytochrome P450 or a fragment thereof. Human antibodies are selected by competitive binding experiments, or otherwise, to have the same epitope specificity as a particular mouse antibody, such as MAb 292-2-3, MAb 763-15-5, MAb 763-15-20, MAb 592-2-5, MAb 5-7-5, MAb 5-1-5, and MAb 281-1-1. Such antibodies are particularly likely to share the useful functional properties of the exemplified antibodies.

3. Antibody Fragments

Antibodies of the invention include intact antibodies and fragments. Typically, these fragments compete with the intact antibody from which they were derived for specific binding to a particular human cytochrome P450 2C family member, and bind with an affinity of at least $10^6$, $10^7$, $10^8$, $10^9$, or $10^{10}$ $M^{-1}$. Antibody fragments include separate heavy chains, light chains Fab, Fab' F(ab')$_2$, $F_v$, and single chain antibodies comprises a heavy chain variable region linked to a light chain variable region via a peptide spacer. Fragments can be produced by enzymic or chemical separation of intact immunoglobulins. For example, a F(ab')$_2$ fragment can be obtained from an IgG molecule by proteolytic digestion with pepsin at pH 3.0–3.5 using standard methods such as those described in Harlow and Lane, supra. Fab fragments may be obtained from F(ab')$_2$ fragments by limited reduction, or from whole antibody by digestion with papain in the presence of reducing agents. (See id.) Fragments can also be produced by recombinant DNA techniques. Segments of nucleic acids encoding selected fragments are produced by digestion of full-length coding sequences with restriction enzymes, or by de novo synthesis. Often fragments are expressed in the form of phage-coat fusion proteins. This manner of expression is advantageous for affinity-sharpening of antibodies.

4. Recombinant Expression of Antibodies

Nucleic acids encoding light and heavy chain variable regions, optionally linked to constant regions, are inserted into expression vectors. The light and heavy chains can be cloned in the same or different expression vectors. The DNA segments encoding antibody chains are operably linked to control sequences in the expression vector(s) that ensure the expression of antibody chains. Such control sequences include a signal sequence, a promoter, an enhancer, and a transcription termination sequence. Expression vectors are typically replicable in the host organisms either as episomes or as an integral part of the host chromosome.

*E. coli* is one procaryotic host particularly for expressing antibodies of the present invention. Other microbial hosts suitable for use include bacilli, such as Bacillus subtilus, and other enterobacteriaceae, such as Salmonella, Serratia, and various Pseudomonas species. In these prokaryotic hosts, one can also make expression vectors, which typically contain expression control sequences compatible with the host cell (e.g., an origin of replication) and regulatory sequences such as a lactose promoter system, a tryptophan (trp) promoter system, a beta-lactamase promoter system, or a promoter system from phage lambda.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

Mammalian tissue cell culture can also be used to express and produce the antibodies of the present invention (see Winnacker, From Genes to Clones (VCH Publishers, N.Y., 1987). Eukaryotic cells are preferred, because a number of suitable host cell lines capable of secreting intact antibodies have been developed. Preferred suitable host cells for expressing nucleic acids encoding the immunoglobulins of the invention include: monkey kidney CV1 line transformed by SV40 (COS-7, ATCC CRL 1651); human embryonic kidney line (293) (Graham et al., J. Gen. Virol. 36:59 (1977)); baby hamster kidney cells (BHK, ATCC CCL 10); Chinese hamster ovary-cells-DHFR (CHO, Urlaub and Chasin, Proc. Natl. Acad. Sci. (USA) 77:4216 (1980)); mouse sertoli cells (TM4, Mather, Biol. Reprod. 23:243–251 (1980)); monkey kidney cells (CV1 ATCC CCL 70); African green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather et al., Annals N.Y. Acad. Sci. 383:44–46 (1982)); baculovirus cells.

The vectors containing the polynucleotide sequences of interest (e.g., the heavy and light chain encoding sequences and expression control sequences) can be transferred into the host cell. Calcium chloride transfection is commonly utilized for prokaryotic cells, whereas calcium phosphate treatment or electroporation can be used for other cellular hosts. (See generally Sambrook et al., Molecular Cloning: A Laboratory Manual (Cold Spring Harbor Press, 2nd ed., 1989) (incorporated by reference in its entirety for all purposes). When heavy and light chains are cloned on separate expression vectors, the vectors are co-transfected to obtain expression and assembly of intact immunoglobulins. After introduction of recombinant DNA, cell lines expressing immunoglobulin products are cell selected. Cell lines capable of stable expression are preferred (i.e., undiminished levels of expression after fifty passages of the cell line).

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see generally Scopes, Protein Purification (Springer-Verlag, N.Y., 1982). Substantially pure immunoglobulins of at least about 90 to 95% homogeneity are preferred, and 98 to 99% or more homogeneity most preferred.

5. Screening for Sequence Analog

Many of the antibodies described above can undergo non-critical aminoacid substitutions, additions or deletions in both the variable and constant regions without loss of binding specificity or effector functions, or intolerable reduction of binding affinity (i.e., below about $10^6$ M$^{-1}$) for human cytochrome P450 2C family members. Usually, the light and heavy chain variable regions of immunoglobulins incorporating such alterations exhibit at least 80, 90 or 95% sequence identity to the corresponding regions of a reference immunoglobulin from which they were derived, such as MAb 292-2-3, MAb 592-2-5, MAb 5-7-5, MAb 5-1-5 and MAb 281-1-1. Preferred antibody light and heavy chain sequence variants have the same complementarity determining regions (CDRs) as the corresponding chains from one of the above reference antibodies. Occasionally, a mutated immunoglobulin can be selected having the same specificity and increased affinity compared with a reference immunoglobulin from which it was derived. Phage-display technology offers powerful techniques for selecting such immunoglobulins. See, e.g., Dower et al., WO 91/17271 McCafferty et al., WO 92/01047; Huse, WO 92/06204.

C. Other Binding Agents of the Invention

The invention further provides nonantibody binding agents that compete with one of the exemplified antibodies for binding to particular human cytochrome P450 2C family members. These binding agents include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980. The libraries of compounds are screened for binding to human cytochrome P450 in competition with one of the reference antibodies MAb 292-2-3, MAb 592-2-5, MAb 5-7-5, MAb 5-1-5 and MAb 281-1-1.

II. Human Cytochrome P450 2C Family

The cDNA for the human cytochrome P450 2C family members has been cloned, sequenced, and expressed. Sources of other cytochromes P450 (e.g., for use in testing for lack of crossreactivity) are described by Nebert, DNA & Cell Biol. 10, 1–14 (1991); Nelson et al., Pharmacogenetics 6, 1–42 (1996). Insect cells (e.g., SF9) with appropriate vectors, usually derived from baculovirus, are also suitable for expressing 2C family members and other cytochromes P450. See Luckow et al., Bio/Technology 6:47–55–55 (198); Gonzalez et al., Meth. Enzymol., 206, 93–99 (1991) (incorporated by reference for all purposes). Other expression systems include yeast (Ellis et al., supra), *E. coli* (Gillam et al., Archives Biochem. Biophys. 319, 540–550 (1995); vaccinia virus (Gonzalez, Pharmacol. Res. 40, 243 (1989), and human AHH-1 lymphoblastoid cells (Crespi et al., Carcinogenesis 10, 295–301 (1989)).

III. Methods of Use

A. Identifying Compounds Metabolized by Particular 2C Family Members

Binding agents of the invention that inhibit enzymic activity of human cytochrome P450 2C family members can be used to assay whether compounds are metabolized by 2C family members. Compounds include xenobiotics, such as a currently used and new drugs, carcinogens, pesticides or other industrial or environmental chemicals, or any endobiotic, such as a steroid hormone. The assay can indicate not only that a compound is metabolized by a particular 2C family member but also the contribution of the particular 2C family member to metabolizing the compound relative to other cytochromes P450 present in microsomes or cell homogenates.

Assays are performed by contacting a compound under test with a particular human cytochrome P450 2C family member in reaction mixtures containing varying amounts of a binding agent of the invention. For example, two separate reactions may be set up, one in which the binding agent of the invention is present, and the other, a control in which the binding agent is absent. The human cytochrome P450 is often present as a microsomal extract from human or animal cells or cell lines or an extract from cell cultures expressing a collection of recombinant P450s including the particular 2C family member. The assay is performed under conditions in which the particular 2C family member is known to be active on known substrates, such as phenanthrene (see Examples). Metabolism of the compound under test is then followed from the disappearance of the compound or appearance of a metabolic product of the compound as a function of time (e.g., nmol product/sec). See, e.g., Buters et al., Drug Metab. Dispos. 22, 688 (1994). The metabolism of the compound is analyzed as a function of the amount of binding agent present. If the metabolism quantitatively decreases with amount of binding agent, it can be concluded that the particular 2C family member metabolizes the compound.

The percentage inhibition of a particular 2C family member catalyzed metabolism of a test compound reflects both the inherent efficiency of a binding agent in blocking the 2C family member activity and thus the contribution of cytochromes P450 other than the particular 2C family member in metabolizing the compound. The inherent blocking efficiency of a binding agent can be determined by measuring inhibition of metabolism in a reaction mixture in which only a particular 2C family member is present, or alternatively, in a reaction mixture in which a collection of cytochromes P450 are present but the substrate is known to be metabolized only by the particular 2C family member. Comparison of the percentage inhibition determined in these circumstances with the percentage inhibition of metabolism of a test substrate when a mixture of cytochromes P450 are present indicates the relative contributions of the particular 2C family member and other enzymes in the mixture to metabolism of the test substrate. For example, if metabolism of a control substrate by pure 2C8 is inhibited by a binding agent by 90% and metabolism of a test substrate by a mixture of cytochromes P450 including 2C8 is inhibited 45%, it can be concluded that in the mixture, 2C8 contributes about 45/90=50% of metabolizing activity on the test substrate. Binding agents having a high degree of inhibition (e.g., at least about 90%) of a known substrate are particularly effective for quantitative analysis as described above.

Information made available by the above methods can be exploited in a number of applications. Drugs determined to be processed by individual 2C family members should in general not be prescribed to patients with PM phenotypes, or should be prescribed in reduced amounts or with close monitoring. Particular caution is needed in combination therapies involving two drugs metabolized by the 2C pathways. The information can also be valuable in drug design and screening. That is drugs can be esigned or screened such that they are metabolized to a significant extent by several P450 enzymes, and are not therefore likely to cause side effects in those deficient in any single enzymes. Recognition that a carcinogen or other environmental toxin is deactivated by a particular 2C family member signals that poor metabolizers are at particular risk from the carcinogen or compound. Conversely, recognition that a carcinogen or other environmental toxin is activated to harmful form by a 2C family member indicates that poor metabolizers are less prone to harm from exposure to such a compound relative to extensive metabolizers.

B. Use of Agents for Identifying Drugs That can be Used for Diagnosing PM Phenotype The binding agents are useful diagnostics to determine a patient's metabolic profile prior to treatment with a drug known or suspected to be metabolized by a 2C family member. Patients identified as 2C poor metabolizers can be given alternative therapy, a lower dosage or additional monitoring to avoid damaging side effects from their PM phenotype. Diagnosis can be performed by two assays, which are described in turn.

1. Binding Assay

Binding agents of the invention are useful for the quantitative measurement of the amount of individual P450 proteins in a sample, which may contain multiple forms of other P450 proteins. Binding between binding agent and the particular cytochrome P450 2C family member in the sample can be detected by radioimmunoassay, ELISA or immunoblotting (see Harlow and Lane, supra). The type of immunoassay can be tailored to the particular application. In radioimmunoassay, the binding agent of the invention is typically labeled. In ELISA, the binding agent is typically unlabelled and detected using a secondary labeled reagent with affinity for the binding agent. Immunoblots are particularly useful for screening a sample with a panel of antibodies to different cytochromes P450.

2. Inhibition Assay

In an inhibition assay, the presence or absence of a particular 2C family member in a tissue sample from a patient is determined from the capacity of a binding agent of the invention to inhibit metabolism of a known substrate of the 2C family member by the tissue sample. A series of reaction mixtures are prepared each of which contains an aliquot of tissue sample from a patient being diagnosed and a known substrate of the particular 2C family member (e.g., phenanthrene). The tissue sample can be obtained from any tissue in which the particular 2C family member is normally expressed, such as the liver. The reaction mixtures differ in the amount of binding agent of the invention present, and a control is usually included in which no binding agent is present. The binding agent used should be one that is known to inhibit the particular 2C family member metabolism. The reaction conditions are such that the known substrate is metabolized to a detectable extent in the control if the tissue sample is from an extensive metabolizer. The rate of substrate metabolism is determined in the reaction mixtures and analyzed as a function of amount of binding agent present. If the tissue sample is from an extensive metabolizer, extensive metabolic activity should be observed in the control in which no inhibitor is present, and decreasing activity should be observed in other reaction mixtures as the amount of binding agent is increased. Conversely, if the sample is from a poor metabolizer, only background metabolic activity (attributable mainly to metabolism of the substrate by other cytochromes P450) is observed in the control, and similar levels of activity are observed in the other reaction mixtures. The lack of correlation between metabolism of substrate and amount of binding agent present signals that the tissue sample is from a poor metabolizer.

C. Other Uses

The binding agents of the invention can also be used for affinity purification of particular cytochrome P450 2C family members. The basic procedure for affinity purification requires only one or two steps and can yield highly purified milligram quantities of a particular cytochrome P450 2C family member. For example, the binding agent can be covalently bound to Sepharose™, which is made into the form of either column or a slurry for batch purification. A sample containing a particular cytochrome P450 2C family member is them passed through the column or slurry and binds to the binding agent-linked Sepharose™. The non-bound material containing unrelated proteins and cytochromes P450 other than the particular 2C family member are thoroughly eluted leaving the cytochrome P450 2C family member of interest, which can then be eluted and used for a variety of chemical and physical studies. See, e.g., Cheng et al., *J Biol. Chem.* (1948) 259: 12279–12284.

Monoclonal antibody based immunohistochemical methods can be applied to localize and examine the distribution of various cytochrome P450 2C family members after different inducer administration, during various physiological states related to nutrition, age, and sex, and in different species and tissues. Furthermore, the intracellular distribution of each cytochrome P450 2C family member can be determined in a way not possible by standard biochemical methods which generally cannot identify the presence of specific forms of cytochrome P450 proteins in isolated tissues and organelles. See, e.g., Gelboin, *Pharmacol. Rev.* 45: 413–453 (1993); Forkert et al., *Res Commun Chem Pathol Pharmacol.* (1986) 53: 147–57; Forkert et al., *Carcinogenesis* (1991) 12: 2259–2268; and Forkert, et al., *Mol. Pharmacol.* (198) 34: 736–43; these references and the references cited therein are herein incorporated by reference.

EXAMPLES

Materials and Methods

Hybridoma Production

The P450 2C9*2 was expressed using a vaccinia vector in Hep G2 cells (Battula et al. 1987) or from a baculovirus vector in insect cells (Gonzalez et al. 1991) and extracted according to published methods (Gelboin et al. 1998). The extracted P450 baculovirus expressed P450 2C9*2 which was used as the immunogen. The vaccinia expressed P450s were used for some of the enzyme analysis. Balb/c mice were immunized with 50 ug of baculo-expressed P450 for three weeks, the spleen cells isolated and fused with myeloma cells (NS-1). The resulting hybridomas were screened for antibody production and binding specificity to single expressed human P450 by ELISA as previously described (Gelboin et al. 1998). Of 1086 hybridomas screened for antibody production and binding specificity one was found to bind specifically to P450 2C9*2. All the other hybridomas yielded MAbs that were either non-binding or not specific to the target P450. The hybridoma producing the desired MAb 292-2-3 was cloned three times, and the MAb was produced in cell culture or by ascites production in mice as described (Gelboin et al. 1998). Other single clones of the 1086 clones that were screened bound to the 2C9 alleles, 2C18 and 2C19, respectively. 830 individual clones were screened to obtain the 2C8 MAbs (MAbs 281-1-1 and 5-1-5). (See Gelboin, H. V., et al. (1998) *Monoclonal Antibodies to Cytochrome P450.* In *Methods in Molecular Biology: Cytochrome P450 Protocols*, edited by I. R. Phillips and E. A. Shephard (New Jersey: Humana Press Inc.), pp. 227–237; this reference and all references cited therein are herein incorporated by reference).

Immunoassays

ELISA was performed on ninety-six well plates which were coated with 1.5 picomole of a single P450. MAbs derived from culture fluids or by diluted ascites fluid were applied and incubated at room temperature for 2 hours. After washing, labeled antibody (alkaline phosphatase goat anti mouse $IgG_{Fc}$) was applied for 1 hour. After washing, the wells were developed with the appropriate substrate (p-nitrophenyl phosphatase) and the absorbance was measured at 405 nm. SDS-PAGE gels and Immunoblots (IB) were performed as previously described (Gelboin et al. 1998).

Immunoinhibition studies were performed using cDNA vaccinia expressed P450 enzymes from Hep G2 cells, Supersomes (Gentest Corp.) and/or Baculosomes (Panvera Corp.). Generally the incubations contained: 30–60 µg of ascites protein containing the MAb which was pre-incubated with 30–50 pmole of P450 enzyme in 0.5 ml in buffer (100 mM Tris pH 7.5) and incubated at 37*C for 5 minutes. The substrate in 10 µl methanol, NADPH, and additional buffer were added to a final volume of 1.0 ml. The incubation was for 30 minutes (60 mm. for tolbutamide) and the metabolites were extracted with 8m1 DCM. Phenanthrene (200 uM) was used for examining the specificity of inhibition of the target P450s by the MAb (Shou et al. 1994). Phenanthrene metabolism was catalyzed by: 1A1, 1A2, 2A6, 2B6, 2C8, 2C9(*1), 2C9(*2), 2C9(*3), 2C18, 2C19, 2E1, 3A4, and 3A5. Burfurolol (50 uM) metabolism was used for measuring 2D6 metabolism (Gelboin et al. 1997). Diclofenac (50 uM) (Crespi and Penman 1997) and Tolbutamide (200 uM) (Relling et al. 1990) were used for testing the specificity of the MAb 292-2-3 inhibition of metabolism catalyzed by each of the three 2C9 allelic variants; 2C9*1, 2C9*2, and 2C9*3. Metabolites formed were separated by HPLC performed using a Hewlett Packard Model 1050 Series system equipped with an autosampler, a ternary solvent delivery system, and a dioarray detector controlled by the Hewlett Packard Chemstations software. Metabolite retention times were compared with authentic standards and metabolite peaks were quantitated based on their ratios to internal standards. Control incubations contained an MAb against hen egg white lysozyme (MAb HyHel-9)(Gelboin et al. 1998). Percent of control metabolism was calculated from that observed with the absence and presence of the MAb 292-2-3.

Human Liver Microsomes and cDNA-expressed P450s

Human liver specimens, stored at −80° C. until use, were obtained from organ donors after clinical death (The NCI Cooperative Human Tissue Network, NIH, Bethesda, Md.). Microsomes were prepared as described (Alvares et al., 1970) and microsomal protein (Lowry et al., 1951) and P450 content (Omura and Sato, 1964) were measured according to published methods.

MAbs Inhibition of 2C Activity

Inhibition of P450 catalyzed activity was always performed with saturating levels of MAbs yielding maximum inhibition. A typical assay contained MAbs in 5 to 25 µL of ascites with a content at about 400 pmol MAb (IgG). This ascites fluid was preincubated with 25 pmol of a particular 2C family member or 250 pmol of human liver microsomal P450s in 0.5 mL of 50 mM potassium phosphate buffer (KPi, pH7.4) at 37° C. for 5 min. The mixture was diluted with the buffer to a final volume of 1 mL. The substrate, i.e., diazepam, tolbutamide, taxol, bufuralol, and phenanthrene, was dissolved in 10 mL of methanol and added (final concentration at 200 µM), and the reaction was initiated by the addition of NADPH (1 mM) at 37° C. Anti-lysozyme MAb (HyHel, IgG), with an amount equivalent to the test MAbs, was used as a control for nonspecific inhibition. Reactions were incubated for 30 min and terminated with 1 mL of acetone. Samples were extracted twice with 7 mL dichloromethane and were dried under N2 and the residue dissolved in mobile phase and immediately analyzed by reversed phase HPLC. The metabolites formed were identified by comparing their retention times with authentic standards.

High Performance Liquid Chromatography

HPLC was performed using a Hewlett-Packard (HP, Rockville, Md., USA) Model HP1050 liquid chromatography system equipped with an HP model 1050 autosampler, a ternary solvent delivery system, and a multiple-wavelength or dioarray detector, which are controlled by the HPLC 2D or 3D ChemStation software installed on a Compaq Deskpro 5133 personal computer (Compaq Computer Cor., Houston, Tex., USA).

Analysis of diazapam metabolism and phenanthrene metabolism (Shou et al., 1994) were previously described, respectively.

RESULTS

Preparation of MAbs Specific to Human P450 2C8, 2C9, 2C18, and 2C19

P450 2C9*2 was expressed using a vaccinia vector in Hep G2 cells (Battula et al. 1987) or from a baculovirus vector in insect cells (Gonzalez et al. 1991) and extracted according to published methods (Gelboin et al. 1998). The extracted P450 baculovirus expressed P450 2C9*2 which was used as the immunogen. The vaccinia expressed P450s were used for some of the enzyme analysis. Balb/c mice were immunized with 50 ug of baculo-expressed P450 for three weeks, the spleen cells isolated and fused with myeloma cells (NS-1). The resulting hybridomas were screened for antibody production and binding specificity to single expressed human P450 by ELISA as previously described (Gelboin et al. 1998). Of 1086 hybridomas screened for antibody production and binding specificity one was found to bind specifically to P450 2C9*2. All the other hybridomas yielded MAbs that were either non-binding or not specific to the target P450. The hybridoma producing the desired MAb 292-2-3 was cloned three times, and the MAb was produced in cell culture or by ascites production in mice as described (Gelboin et al. 1998).

FIG. 1 shows the immunoblot analysis of the specificity of the five MAbs to human P450 2C8, 2C9*2, 2C18, and 2C19. MAbs 292-2-3 did not form an immunoblot with any 2C family members. MAb 281-1-1 yielded an immunoblot only to the target 2C8 and not to the other cytochrome P450 2C family members. MAb 592-2-5 formed an immunoblot with 2C9 and 2C18. MAb 5-7-5 yielded strong immunoblots with all three 2C9 alleles and a weak to moderate immunoblot to 2C8, 2C18, and 2C19.

FIG. 4 shows the specificity analysis of MAb 292-2-3, MAb 592-2-5, MAb 5-7-5, MAb 5-1-5, and MAb 281-1-1 to human P450 2C family members. Immunoblots, ELISA, and inhibition results are shown. MAb 292-2-3 shows a positive ELISA for 2C9*1, 2C9*2, and 2C9*3 while MAb 592-2-5 shows a positive ELISA for 2C9*2 and a weak ELISA for 2C18. MAb 5-7-5 shows a positive ELISA for 2C9*1, 2C9*2, and 2C9*3, 2C18 and 2C19 while both MAb 5-1-5 and MAb 281-1-1 show a moderate ELISA for 2C8.

The immunobinding and ELISA data of MAb 281-1-1, MAb 592-2-5, 5-1-5, and MAb 5-7-5 show that these MAbs are highly specific to 2C8, or 2C9*1, 2C9*2, and 2C9*3, 2C18, and 2C19.

Inhibitory Activity of MAb 292-2-3, Mab 5-1-5, MAb 592-2-5, MAb 281-1-1, and MAb 5-7-5 Toward 2C8, 2C9*2, 2C18, and 2C19 Enzyme Activity The metabolism of two substrates of the 2C family members, phenanthrene (FIG. 2) (Shou et al., 1994) or diazepam (FIG. 3)were used to measure the inhibitory activity of the MAbs. The data show the inhibitory activity of the MAbs toward the 2C family-catalyzed metabolism. The inhibition of phenanthrene metabolism ranged from 82–96%. The inhibition of diazepam metabolism ranged from 66–93%. The five MAbs shown are thus sensitive and precise probes for measuring 2C-catalyzed metabolism in liver and other tissues.

Specificity of Binding of MAb 292-2-3 to Expressed Human P450 2C9 Alleles

The specificity of binding of the MAb 292-2-3 to the expressed P450 family members determined by ELISA is shown in FIG. 5. The MAb 292-2-3 binds only to the single expressed 2C9*2 and does not bind the wild type 2C9*1 or the 2C9*3. Further, the MAb 292-2-3 does not bind to other members of the 2C family, 2C8, 2C18, 2C19 and none of the non-2C isoforms of human liver P450s, i.e., 1A1, 1A2, 2A6, 2B6, 2D6, 2E1 or 3A4/5. The MAb 292-2-3 does not immunoblot any of the above three 2C9 alleles.

Figure 6:
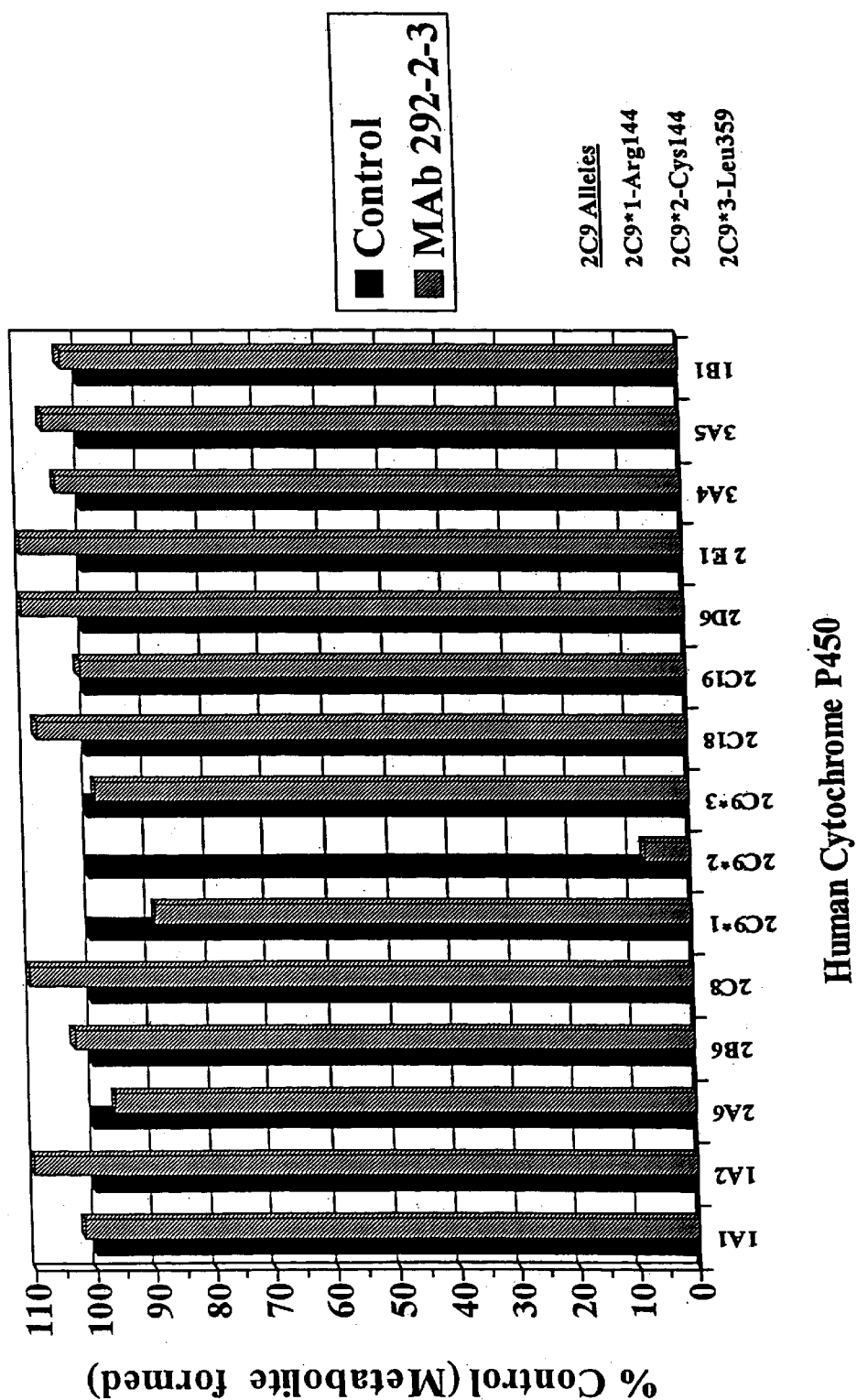
FIG. 6. Specificity of MAb 292-2-3: Inhibition of Metabolism by P450 2C9 Alleles and Other P450 Family Members.

FIG. 6 shows the specificity of inhibition of MAb 292-2-3 for the metabolism of phenanthrene catalyzed by the 2C9*1 and 2C9*2 alleles and other P450 isoforms in human liver except for 2D6 measured by bufuralol metabolism and 2C9*3 measured by diclofenac metabolism. The metabolism by 2C9*2 was inhibited by at least 90% by MAb 292-2-3 which exhibited no significant inhibition of the two other 2C9 alleles, 2C isoforms (8, 18, 19) or the non 2C /P450 isoforms, 1A1, 1A2, 2A6, 2B6, 2C8, 2D6, 2E1, 3A4 or 3A5. All of the measurements of enzyme activity and inhibition by the MAbs were performed with P450s expressed from either vaccinia or baculovirus vectors.

The specificity of MAb 292-2-3 toward each of the three 2C9 allele catalyzed metabolism of two major 2C9 substrates, tolbutamide and diclofenac, is shown in FIG. 7. The MAb 292-2-3 inhibited 2C9*2 by more than 95% and did not exhibit significant inhibition of the P450 2C9*1 or 2C9*3.

Figure 8:
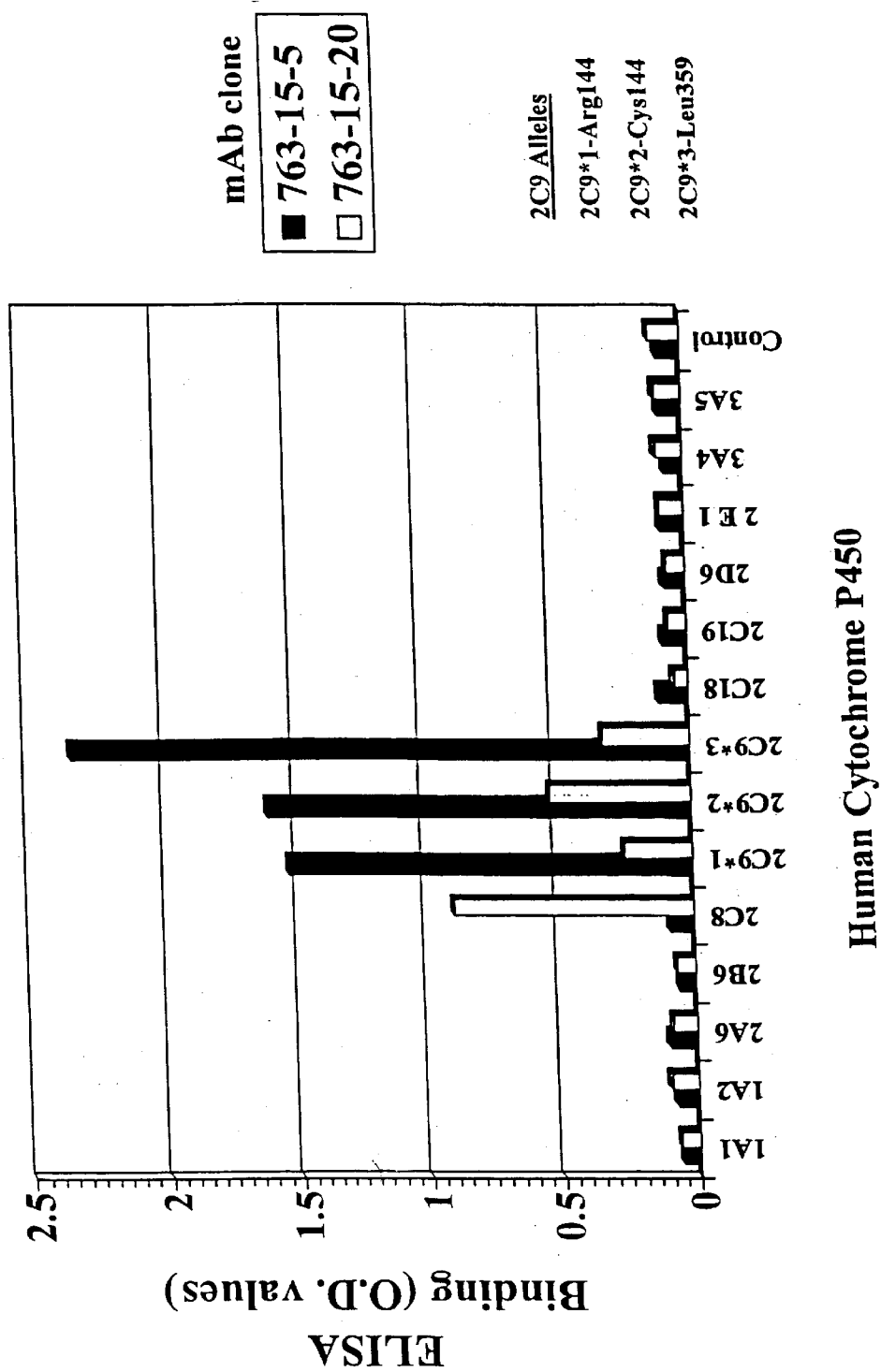
FIG. 8. Specificity of Binding of MAb 763-15-5 and MAb 763-15-20 to Expressed Human P450 Family Members.
Figure 9:
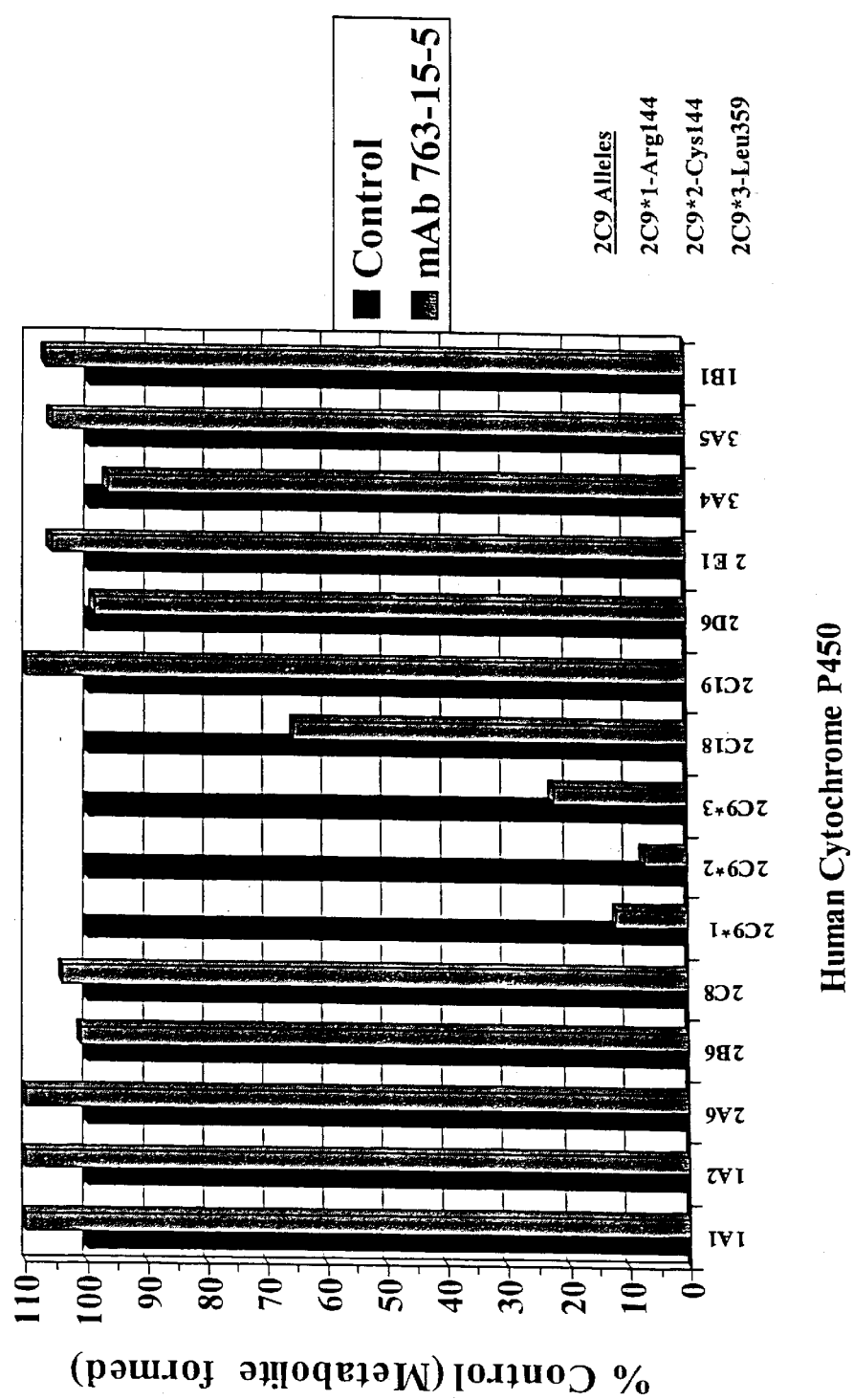
FIG. 9. Specificity of MAb 763-15-5: Lack of Inhibition of Other Human P450 Family Members.

Specificity of Binding of MAb 763-15-5 and MAb 763-15-20 to Expressed Human P450 2C9 Alleles The specificity of binding of MAb 763-15-5 and MAb 763-15-20 to the expressed human P450 family members by ELIZA is shown in FIG. 8. FIG. 9 shows the specificity of MAb 763-15-5. MAb 763-15-5 inhibits each of the three 2C9 alleles catalyzed metabolism of one of the major 2C9 substrates. Phenanthrene metabolism was used for all P405s except diclofenac metabolism for the P450 2C9 alleles and bufuralol metabolism for P450 2D6. MAb 763-15-5 inhibited 2C9*2 by more than 90% and inhibited the P450 2C9*1 and 2C9*3 by more than 75%. MAb 763-15-20 inhibited 2C9*2 by more than 10% and did not exhibit significant inhibition of the P450 2C9*1 or 2C9*3.

Figure 10:
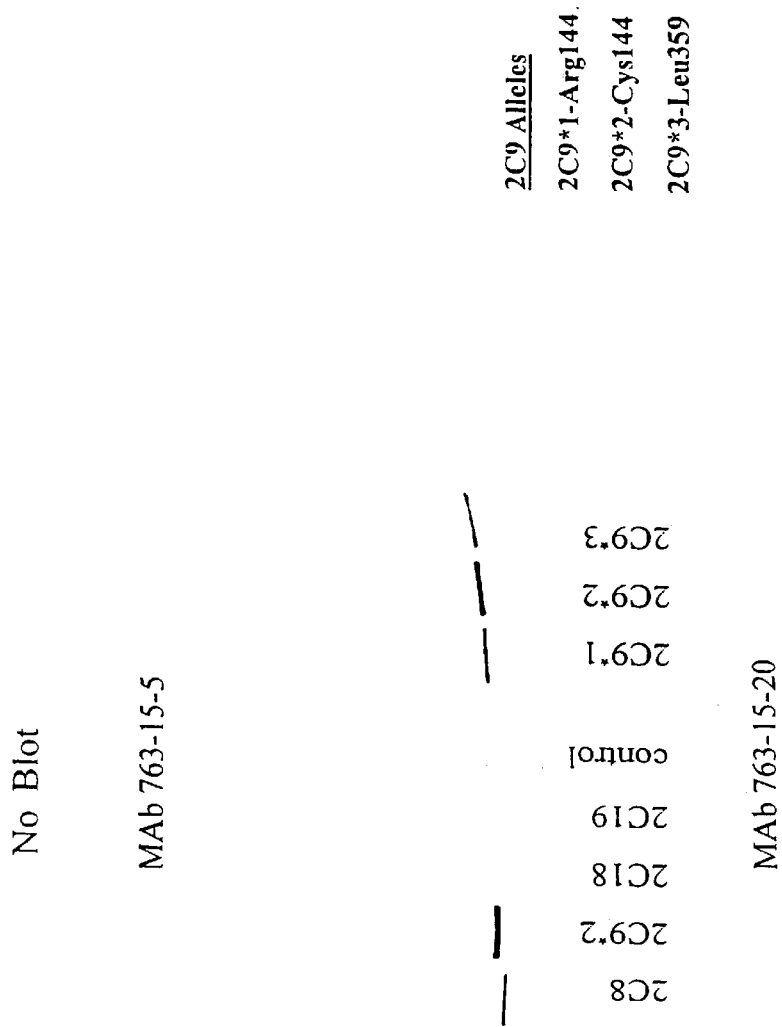
FIG. 10. Immunoblot Analysis of MAb 763-15-5 and MAb 763-15-20.

The immunoblot analysis of MAb 763-15-5 and MAb 763-15-20 is shown in FIG. 10 MAb 763-15-5 did not yield an immunoblot whereas MAb 763-15-20 bound strongly to human P450 2C8 and all three allelic variants of human P450 2C9.

FIG. 11 shows the inhibition of P450 2C9 allele metabolism of diclofenac by MAb 763-15-5 and MAb 763-15-20. MAb 763-15-5 inhibited 2C9*2 metabolism of diclofenac by m ore than 90% and inhibited the P450 2C9*1 and 2C9*3 by more than 75%. MAb 763-15-20 inhibited 2C9*2 metabolism of diclofenac by more than 10% and did not exhibit significant inhibition of the P450 2C9*1 or 2C9*3.

REFERENCES

Battula, N., Sagara, J., Gelboin, H. V., 1987, Expression of P1-450 and P3-450 DNA coding sequences as enzymatically active cytochromes P-450 in mammalian cells, *Proceedings of the National Academy of Sciences USA*, 12, 4073–4077.

Crespi, C. L., Penman, B. W., 1997, Use of eDNA-Expressed Human Cytochrome P450 Enzymes to Study Potential Drug-Drug Interactions, *Advances in Pharmacology*, 43, 171–188.

Forkert, P. G., Vessey, M. L., Elce, J. S., Park, S. S., Gelboin, H. V., Cole, S. P., 1986, Localization ofphenobarbital- and 3-methylcholanthrene-inducible cytochromes P-450 in mouse lung with monoclonal antibo dies, *Res Commun Chem Pathol Pharmacol.* 53, 147–57.

Forkert, P. G., Mirehouse-Brown P., Park S. S., Gelboin H. V., (198), Distribution and induction sites of phenobarbital- and 3-methylcholanthrene-inducible cytochromes P-450 in murine liver: immunohistochemical localization with monoclonal antibodies. Mol. Pharmacol., 34, 736–43.

Forkert P. G., Massey T. E., Jones A. B., Park S. S ., Gelboin H. V., Anderson L. M. (1991), Distribution of cytochrome CYP2E1 in murine liver after ethanol and acetone administration, Carcinogenesis 12, 2259–2268.

Fujino, T., Park, S. S., West,. and Gelboin, H. V., 1982, Phenotyping of cytochromes P-450 in human tissues with monoclonal antibodies, *Proceedings of the National Academy of Sciences USA*, 79, 3682–3686.

Gelboin, H. V., 1993, Monoclonal antibodies and cytochrome P450, *Pharmacological Reviews*, 45:413–453.

Gelboin, H. V., Krausz, K. W., Goldfarb, I., Buters, J. T. M., Yang, S. K., Gonzalez, F. J., Korzekwa, K. R. and Shou, M., 1995, Inhibitory and non inhibitory monoclonal antibodies to human cytochrome P450 3A3/4, *Biochemical Pharmacology*, 50, 1841–1850.

Gelboin, H. V., Goldfarb, I., Krausz, K. W., Grogan, J., Korzekwa, K. R., Gonzalez, F. J., and Shou, M., 1996, Inhibitory and non-inhibitory monoclonal antibodies to human cytochrome P450 2E1, *Chemical Research Toxicology*, 9, 1023–1030.

Gelboin, H. V., Krausz, K. W., Shou, M., Gonzalez, F. J. and Yang, T. J., 1997, A monoclonal antibody inhibitory to human P450 2D6: a paradigm for use in combinatorial determination of individual P450 role in specific drug tissue metabolism, *Pharmaco genetics*, 7, 469–477.

Gelboin, H. V., Shou, M., Goldfarb, I., Yang, T. J. and Krausz, K. W., 1998, Monoclonal Antibodies to Cytochrome P450. In Methods in Molecular Biology: Cytochrome P450 Protocols, edited by I. R. Phillips and E. A. Shephard (New Jersey: Humana Press Inc.), pp. 227–237.

Gelboin, H. V., Krausz, K. W., Gonzalez, F. J., and Yang, T. J., 1999, Monoclonal Antibodies and Human Cytochromes P450: A New Avenue for Drug Discovery, In Press.

Gonzalez, F. J., Kimura, S., Tamura, S., Gelboin, H. V., 1991, Expression of mammalian cytochrome P450 using baculovirus, *Methods in Enzymology*, 206, 93–99.

Haining, R. L., Hunter, A. P., Veronese, M. E., Trager, W. F., Rettie, A. E., 1996, Allelic variants of human cytochrome P450 2C9: baculovirus-mediated expression, purification, structural characterization, substrate stereoselectivity, and prochiral selectivity of the wild-type and 1359L mutant forms, *Arch Biochem Biophys*, 333, 447–458.

Ingelman-Sundberg, M., Oscarson, M., McLellan, R. A., 1999, Polymorphic human cytochrome P450 enzymes: an opportunity for individualized drug treatment, *Trends Pharmacol Sci*, 20, 342–349.

Ioannides, C. (Ed) (1996) *Cytochrome P450: Metabolic and Toxicology Aspects*, CRC Press, pp. i-411.

Kaminsky, L. S., De Morais, S. M., Faletto, M. B., Dunbar, D. A., Goldstein, J. A., 1993, Correlation of human cytochrome P4502C substrate specificities with primary structure: warfarin as a probe, *Molecular Pharmacology*, 43, 234–239.

Kohler, G., Milstein, C., 1975, Continuous cultures of fused cells secreting antibody of predefined specificity, *Nature*, 7, 495–497.

Miners, J. O., Birkett, D. J. 1998, Cytochrome P450 2C9: an enzyme of major importance in human drug metabolism, *British Journal of Clinical Pharmacology*, 45, 525–53 8.

Montellano, 0. (Ed) (1995) *Cytochrome P450: Structure, Mechanism and Biochemistry*, Plenum Press, pp. 473–535.

Nasu, K., Kubota, T., Ishizaki, T., 1997, Genetic analysis of CYP2C9 polymorphism in a Japanese population, *Pharmacogenetics*, 7, 405–409

Relling, M. V., Aoyama, T., Gonzalez, F. J., Meyer, U. A., 1990, Tolbutamide and Mephenytoin Hydroxylation by Human Cytochrome P450s in the CYP2C Subfamily, *American Society for Pharmacology and Experimental Therapeutics*, 252, 442–447.

Rendic, S., Di Carlo, F. J., 1997, Human cytochrome P450 enzymes: status report summarizing their reactions, substrates, inducers, and inhibitors, *Drug Metabolism Review*, 29, 413–580.

Rettie, A. E., Wienkers, L. C., Gonzalez, F. J., Trager, W. F., Korzekwa, K. R., 1994, Impaired (S)-warfarin metabolism catalyzed by the R144C allelic variant of CYP2C9, *Pharmacogenetics*, 4, 39–42.

Sai, Y., Yang, T. J., Krausz, K. W., Gonzalez, F. J. and Gelboin, H. V., 1999, An Inhibitory Monoclonal Antibody to Human Cytochrome P450 2A6 Defines its Role in the Metabolism of Coumarin, 7-ethoxycoumarin and 4-nitroanisole in Human Liver, *Pharmacogenetics*, 9, 229–237.

Shou, M., Korzekwa, K. R., Krausz, K. W., Crespi, C. L., Gonzalez, F. J., Gelboin, H. V., 1994, Regio-and Stereo-Selective Metabolism of Phenanthrene by twelve cDNA Expressed Human, Rodent, and Rabbit Cytochromes P450, *Cancer Letters*, 83, 305–313.

Stubbins, M. J., Harries, L. W., Smith, G., Tarbit, M. H., Wolf, C. R., 1996, Genetic analysis of the human cytochrome P450 CYP2C9 locus, *Pharmacogenetics*, 6, 429–439.

Sullivan-Klose, T. H., Ghanayem, B. I., Bell, D. A., Zhang, Z. Y., Kaminsky, L. S., Shenfield, G. M., Miners, J. O., Birkett, D. J., Goldstein, J. A., 1996, The role of the CYP2C9-Leu359 allelic variant in the tolbutamide polymorphism, *Pharmacogenetics*, 6, 341–349.

Tassaneeyakul, W., Birkett, D. J., Veronese, M. E., Mc Manus, M. E., Tukey, R. H., Quattrochi, L. C., Gelboin, H. V., Miners, J. O., 1993, Specificity of substrate and inhibitor probes for human cytochromes P 450 1A1 and 1A2, *Journal of Pharmacology Experimental Therapy*, 1, 401–407.

Vemeulen NPE, 1996, Role of metabolism in chemical toxicity, in C. Ioannides, Ed., Cytochromes P450:metabolic and toxicological aspects, New York, CRC Press, 29–53.

Veronese, M. E., Mackenzie, P. I., Doecke, D. J., McManus, M. E., Minors, J. O., Birkett, D. J., 1991, Tolbutamide and phenytoin hydroxylation's by cDNA-expressed human liver cytochrome P450 2C9, *Biochemical Biophysical Research Comminations*, 175,1112–1118.

Yamazaki, H., Inoue, K., Chiba, K., Ozawa, N., Kawai, T., Suzuki, Y., Goldstein, J. A., Guengerich, F. P., Shimada, T., 1998, Comparative studies on the catalytic roles of cytochrome P450 2C9 and its Cys- and Leu-variants in the oxidation of warfarin, flurbiprofen, and diclofenac by human liver microsomes, *Biochem Pharmacol*, 56, 243–251.

Yang, T. J., Sai, Y., Krausz, K. W., Gonzalez, F. J. and Gelboin, H. V., 1998, Inhibitory Monoclonal Antibodies to Human cytochrome P450 1A2: analysis of phenacetin 0-Deethylation in human liver, *Pharmacogenetics*, 8, 375–382.

Yang, T. J., Krausz, K. W., Shou, M., Yang, S. K., Buters, J. T. M., Gonzalez, F. J. and Gelboin, H. V., 1998, Inhibitory monoclonal antibody to human cytochrome P450 2B6, *Biochemical Pharmacology*, 55, 1633–1640.

Yang, T. J., Krausz, K. W., Sai. Y., Gonzalez, F. J. and Gelboin, H. V., 1999, Eight Inhibitory Monoclonal Antibodies Define the Role of Individual P450s in Human Liver Microsomal Diazepam, 7-Ethoxycoumarin and Imipramine Metabolism, *Drug Metabolism and Disposition*, 27, 102–109.

Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

What is claimed is:

1. A monoclonal antibody that competes with the monoclonal antibody MAb 281-1-1 (ATCC HB-12648) for specific binding to human cytochrome P450 2C8, and that specifically inhibits 2C8-catalyzed metabolism of phenanthrene by at least 50%.

2. The monoclonal antibody of claim 1 that lacks specific binding to each of human cytochromes P450 1A1, 1A2, 2A6, 2B6, 2C9, 2C19, 2D6, 2E1, 3A4, and 3A5.

3. The monoclonal antibody of claim 1 that specifically inhibits 2C8-catalyzed metabolism of phenanthrene by at least 90%.

4. The monoclonal antibody of claim 1 that is a mouse antibody.

5. The monoclonal antibody of claim 1, wherein the light chain variable domain comprises three complementarity determining regions (CDRs) from the light chain of the monoclonal antibody MAb 281-1-1 (ATCC HB-12648), and the heavy chain variable domain comprises three complementarity determining regions (CDRS) from the heavy chain of the monoclonal antibody MAb 281-1-1-1 (ATCC HB-12648).

6. The monoclonal antibody of claim 1 that is MAb 281-1-1 (ATCC HB-12648) or a binding fragment thereof.

7. A cell line producing the monoclonal antibody of claim 6.

8. The cell line of claim 7 that is a eucaryotic cell line.

9. The cell line of claim 7 that is a procaryotic cell line.

\* \* \* \* \*